United States Patent [19]
Novinkov

[11] Patent Number: 6,093,174
[45] Date of Patent: Jul. 25, 2000

[54] PRE-FILLED SYRINGE WITH MECHANISM TO STORE NEEDLE THEREIN

[76] Inventor: Oleg L. Novinkov, 8950 Chimney Rock, #130, Houston, Tex. 77096

[21] Appl. No.: 09/082,601

[22] Filed: May 21, 1998

[51] Int. Cl.[7] .............................. A61M 5/32; A61M 5/00
[52] U.S. Cl. ........................ 604/195; 604/192; 604/263; 128/919
[58] Field of Search .................................. 604/110, 187, 604/192, 194, 195, 197, 198, 263, 264; 128/909

[56] References Cited

U.S. PATENT DOCUMENTS

| | | |
|---|---|---|
| 720,381 | 2/1903 | Ranger . |
| 3,107,785 | 10/1963 | Roehr . |
| 3,534,734 | 10/1970 | Budreck ................................. 604/194 |
| 4,011,868 | 3/1977 | Friend . |
| 4,390,016 | 6/1983 | Riess . |
| 4,863,433 | 9/1989 | Payne et al. .............................. 604/194 |
| 4,941,883 | 7/1990 | Venturini . |
| 5,112,315 | 5/1992 | Gloyer et al. . |
| 5,248,299 | 9/1993 | Ota .......................................... 604/110 |
| 5,267,973 | 12/1993 | Haber et al. . |
| 5,342,323 | 8/1994 | Haining . |
| 5,658,257 | 8/1997 | Ryles . |

Primary Examiner—Ronald Stright
Assistant Examiner—Michael J. Hayes
Attorney, Agent, or Firm—Keeling Law Firm

[57] ABSTRACT

A pre-filled syringe comprising, as common prior art syringes have, a partially open end, a neck extending therefrom, a needle, a needle cover plus a new type of attachment for storing and using the syringe needle. Prior to using the pre-filled syringe, the needle and needle cover are attached to the inside surface of the syringe neck, with the needle puncture end (and the respective needle cover end) within the syringe body surrounded by the pre-filled solution, while the needle attachment end (and the respective needle cover end) is exterior to the syringe body. To use the syringe, the needle cover and needle are removed from the syringe body interior and are attached at the needle attachment end to the outside surface of the syringe neck. The needle cover is then removed from the needle, and the needle is now primed for use. In one embodiment, the storage attachment comprises mating threading on the needle cover and the body neck. In another embodiment, the storage attachment comprises at least one rib on either the needle cover or the body neck and at least two ribs on the other of the needle cover or the body neck. The ribs provide a snapping engagement between the needle cover and the body neck. After use of the syringe, the needle and cover are re-inserted into the body of the syringe for ultimate disposal.

11 Claims, 2 Drawing Sheets

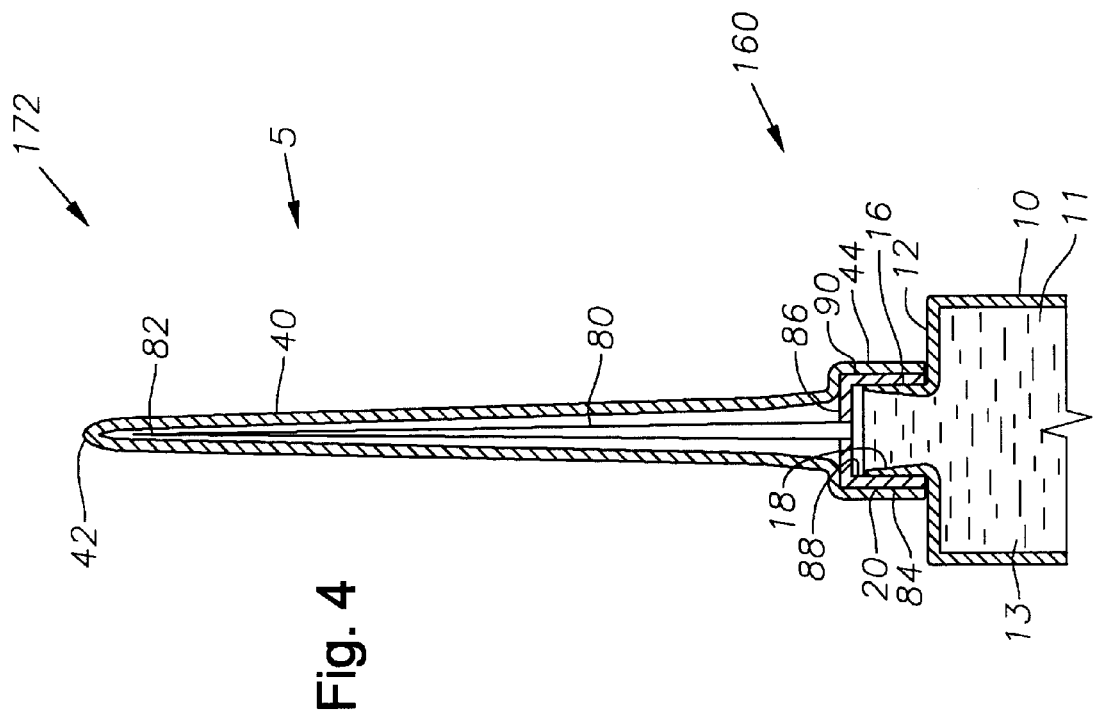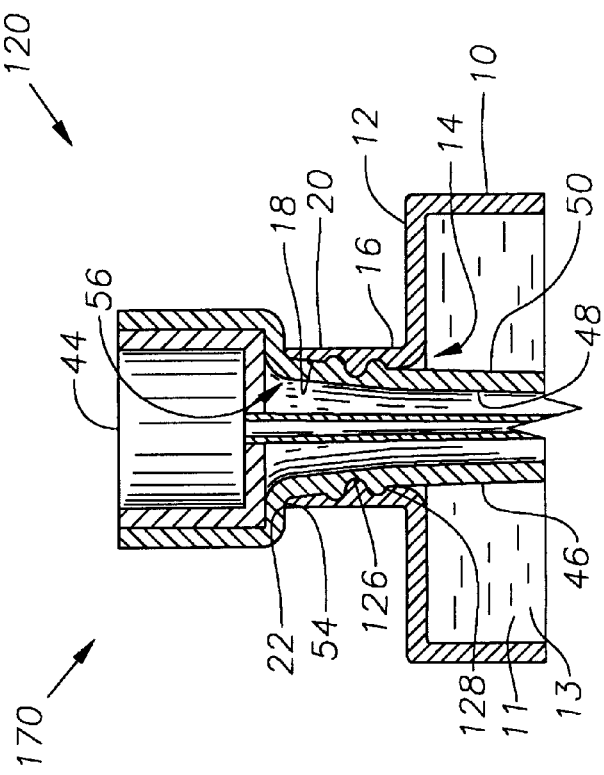

PRE-FILLED SYRINGE WITH MECHANISM TO STORE NEEDLE THEREIN

BACKGROUND OF THE INVENTION

1. Field of Invention

This invention relates generally to syringes. Specifically, this invention relates to syringes that are pre-filled and include a mechanism for storing the syringe's needle within the body of the syringe prior to use of the syringe.

By being attached to the front end of a syringe body, a needle increases the overall size of a syringe. Some syringes are sold pre-filled with a specific amount of medical solution and with the needle already attached to the syringe body at the syringe's front end. These syringes are usually enclosed in a package. Because the needle is already attached to the syringe body, the overall syringe takes up a large amount of space all of which must be enclosed by the package. The conservation of space is important to medical providers. And, in specific instances such as battlefield applications and space flight, the conservation of space is vital.

Thus, it would be beneficial to the prior art to provide a pre-filled syringe which takes up less space than comparable prior art syringes. Specifically, it would be beneficial to the prior art to provide a pre-filled syringe whose overall size prior to use is decreased by not including the ready to use needle to syringe body attachment common in prior art syringes.

Some prior art syringes conserve space by storing the needle within the syringe body prior to the use of the syringe. None of such syringes, however, provide for such storage in a pre-filled syringe. As is widely known, pre-filled syringes are common and useful in the industry. Thus, it would be beneficial to the prior art to provide a pre-filled syringe which includes a storing means for storing the syringe needle within the syringe body prior to use.

In addition, after a syringe is used and its needle is exposed, the exposed needle presents a safety hazard to medical providers. Typically, the used syringe, together with the exposed needle, is disposed of in a "Sharp's Container." Nevertheless, even when they are disposed of in a Sharp's Container, the syringe and needle still pose a safety hazard due to the exposure of the sharp needle. Thus, it would be beneficial to the prior art to provide a safer syringe which, after use, can be disposed of without having the needle exposed therefrom.

2. Related Art

There are a variety of syringes in the prior art which include a needle storage means. Illustrative of such prior art syringes are U.S. Pat. No. 720,381 which issued to Ranger on Feb. 10, 1903; U.S. Pat. No. 3,107,785 which issued to Roehr on Oct. 22, 1963; U.S. Pat. No. 4,011,868 which issued to Friend on Mar. 15, 1977; U.S. Pat. No. 4,390,016 which issued to Riess on Jun. 28, 1983; U.S. Pat. No. 4,941,883 which issued to Venturini on Jul. 17, 1990; U.S. Pat. No. 5,112,315 which issued to Gloyer et al. on May 13, 1992; U.S. Pat. No. 5,267,973 which issued to Haber et al. on Dec. 7, 1993; U.S. Pat. No. 5,342,323 which issued to Haining on Aug. 30, 1994; and U.S. Pat. No. 5,658,257 which issued to Ryles on Aug. 19, 1997.

The storage means of most of the listed patents are not included within the body of the syringe. Thus, in such patents, the storage means itself substantially adds to the overall size of the syringe. Unlike such patents, the Ranger Patent as well as the Roehr Patent disclose syringes which include a needle storage means within the syringe body. However, neither patents discloses the use of such storage means in a pre-filled syringe body. The Riess Patent discloses a syringe which includes a storage means and a pre-filled syringe body. However, in this patent, the storage means is essentially independent of the pre-filled syringe body, and the storage means itself substantially adds to the overall size of the syringe.

SUMMARY OF THE INVENTION

Accordingly, the objectives of this invention are to provide, inter alia, a pre-filled syringe:

that takes up less space than comparable prior art syringes;

whose overall size is decreased by not including the needle to syringe body attachment common in prior art syringes;

that includes a storing means for storing the syringe needle within the syringe body prior to use; and that can be disposed of after use without having its needle exposed therefrom.

Other objects of the invention will become apparent from time to time throughout the specification hereinafter disclosed.

To achieve such improvements, my invention is a pre-filled syringe having, as common prior art syringes have, a partially open end, a neck extending therefrom, and a needle. In addition, however, my syringe includes a needle cover, a storage attachment means, and an operational attachment means. The needle cover is generally in the shape of the needle, and the needle includes a puncture end and an attachment end. When the storage attachment means is engaged, the syringe, its needle, and its needle cover are in the storage position, in which at least a portion, and preferably a majority, of the needle cover is inserted through the body neck opening into the interior of the pre-filled syringe body. The needle is frictionally retained within the needle cover. Storage attachment means selectively and sealingly attaches the needle cover to the inside surface of the syringe neck. In the storage position, the needle puncture end (and the respective needle cover end) is within the syringe body surrounded by the pre-filled solution and the needle attachment end (and the respective needle cover end ) is exterior to the syringe body. When the operational attachment means is engaged, the syringe, its needle, and its needle cover are in their operative position in which the needle, still frictionally retained within the needle cover, is selectively attached (also by friction) at its needle attachment end to the outside surface of the syringe neck. Once the operational attachment means is secured, the needle cover is removed from the needle, and the needle is now primed for use with its puncture end located distal to the syringe body. In one embodiment, the storage attachment means comprises mating threading on the needle cover and the body neck. In another embodiment, the storage attachment means comprises at least one rib on either the needle cover or the body neck and at least two ribs on the other of the needle cover or the body neck. The ribs provide a "snapping" engagement between the needle cover and the body neck.

BRIEF DESCRIPTION OF THE DRAWINGS

FIG. 3 is a cross-sectional view of another embodiment of the storage attachment means, including the needle cover without the needle retained therein.

FIG. 4 is an elevational view of the front section of a clear pre-filled syringe in the operative position.

DETAILED DESCRIPTION OF THE INVENTION

Figure 2:
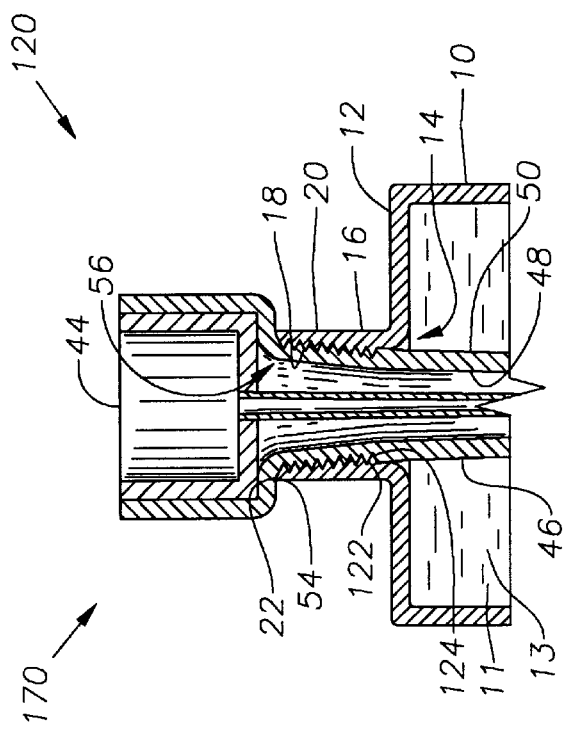
FIG. 2 is a cross-sectional view of one embodiment of the storage attachment means, including the needle cover without the needle retained therein.

The syringe which is the subject of this application is shown generally in FIGS. 1–4 as reference numeral 5. Syringe 5 comprises a syringe body 10, a needle 80, a needle cover 40, a storage attachment means 120, and an operational attachment means 160. Syringe body 10 is comparable to prior art syringe bodies. Importantly, syringe body 10 is pre-filled with solution 11. Prior to use, needle 80 is stored within needle cover 40. Storage attachment means 120 selectively sealingly attaches needle cover 40 (and needle 80 therein) to pre-filled syringe body 10 so that at least a portion of needle cover 40 (and needle 80 therein) is within the interior 13 of syringe body 10. Operational attachment means 160 selectively attaches needle 80 to syringe body 10 for operation of syringe 5.

Figure 1:
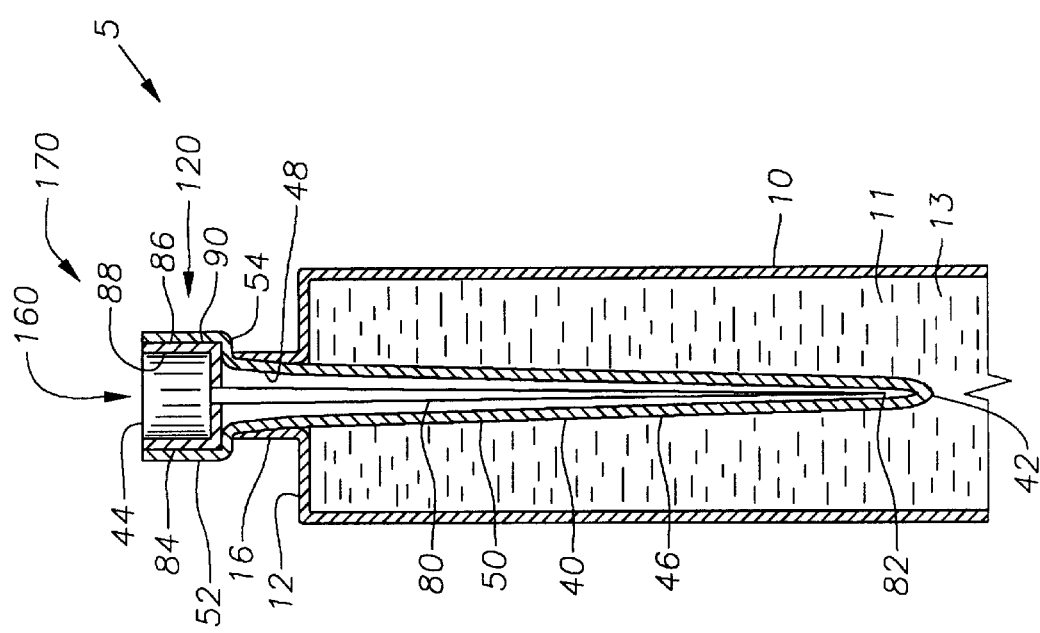
FIG. 1 is an elevational view of the front section of a clear pre-filled syringe in the storage position.

When storage attachment means 120 is engaged, syringe 5 and needle cover 40 are in the storage position 170. Storage position 170 is illustrated in FIGS. 1–3 and will be more fully described herein. When operational attachment means 160 is engaged, syringe 5 and needle cover 40 are in operative position 172. Operative position 172 is illustrated in FIG. 4 and will also be more fully described herein.

As shown in the Figures, syringe body 10 is comparable to prior art syringe bodies. It is thus understood that syringe body 10 includes a hollow interior 13 and may include the normal plunger and seal mechanism of prior art syringes. As an alternative, syringe body 10 may comprise the structure of the syringe disclosed in this Applicant's co-pending U.S. patent application Ser. No. 09/047,020 entitled Syringe and Method of Using Same and filed on Mar. 24, 1998. In any event, syringe body 10 is hollow and includes a partially enclosed body end 12. Preferably concentric therewith, body end 12 includes a body opening 14 which provides fluid communication between the interior 13 of syringe body 10 and the exterior of syringe body through needle 80, as is well known in the art. In the preferred embodiment, body opening 14 has a circular cross-sectional area.

Syringe body 10 further includes a body neck 16. Body neck 16 extends from the perimeter of body opening 14 in a direction away from syringe body 10. In the preferred embodiment, body neck 16 extends in a direction perpendicular to body end 12. Body neck 16 includes an inner surface 18 and an outer surface 20. Preferably, body neck 16 is cylindrical in shape having a circular cross-sectional area. Body neck 16 includes a body neck front surface 22 located distal syringe body 10.

Needle 80 comprises a common prior art needle. For purposes of description, needle 80 includes a puncture end 82 and an attachment end 84. Needle attachment end 84 typically includes a needle cylinder 86 which has an inner surface 88 and an outer surface 90. Needle 80 provides fluid communication between the interior 13 of syringe body 10 and the exterior of syringe body 10.

Needle cover 40 selectively receives needle 80 therein for storage purposes. Preferably, needle cover 40 has the general shape of needle 80. Needle cover 40 includes a needle cover body 46, a first end 42, and a second end 44. Needle cover first end 42 corresponds to and selectively retains and houses needle puncture end 82 when needle 80 is stored within needle cover 40. Needle cover second end 44 corresponds to and selectively retains and houses needle attachment end 84 when needle 80 is stored within needle cover 40. Needle cover first end 42 is enclosed. Needle cover second end 44 is open. Preferably, needle cover 40 is constructed from a material that does not chemically react with the solution 11 located within syringe body 10, such as the same material from which prior art syringe bodies are constructed.

In order to house needle 80 therein, needle cover 40 is hollow thereby defining a cover inner surface 48 and a cover outer surface 50. Needle cover 40 further includes a holding cylinder 52 which houses needle cylinder 86 when needle 80 is stored within needle cover 40. Preferably, holding cylinder 52 is adjacent needle cover second end 44. Holding cylinder 52 defines the largest cross-sectional area of needle cover 40. From holding cylinder 52, needle cover 40 decreases in cross-sectional area at needle cover shoulder 54. From needle cover shoulder 54, the cross-sectional area of needle cover 40 gradually decreases up to needle cover first end 42.

In the preferred embodiment, needle cover 40 and needle 80 are sized and constructed so that needle 80 is selectively frictionally retained within needle cover 40. Preferably, the cross-sectional area of needle cylinder outer surface 90 is substantially equal to the inner cross-sectional area of needle cover holding cylinder 52 thereby producing the frictional retention.

Needle cover 40 further includes a storage attachment segment 56. Storage attachment segment 56 is the portion of needle cover 40 which is selectively attached to syringe body 10 when syringe 5 is in the storage position 170. Storage attachment segment 56 is located on needle cover outer surface 50. In the preferred embodiment, storage attachment segment 56 is located intermediate needle cover shoulder 54 and needle cover first end 42, directly adjacent to needle cover shoulder 54.

As previously disclosed, storage attachment means 120 selectively sealingly attaches needle cover 40 (and needle 80 therein) to syringe body 10. Importantly, storage attachment means 120 provides such attachment so that at least a portion of needle cover 40 is located within pre-filled syringe body 10. Also of importance, the attachment provided by storage attachment means 120 is a sealing attachment which prohibits solution 11 from flowing out of syringe body 10 when storage attachment means 120 is engaged.

Generally, in order to enable the operation of storage attachment means 120, needle cover 40 is inserted into the interior 13 of syringe body 10 so that needle cover first end 42 is directly within syringe body 10 and is surrounded by solution 11, needle cover shoulder 54 is adjacent to but preferably abuts the front surface 22 of body neck 16, needle cover storage attachment segment 56 is directly adjacent to body neck inner surface 18, and needle cover second end 44 is exterior to syringe body 10.

In one preferred embodiment as shown in FIG. 2, storage attachment means 120 comprises threading 122 on body neck inner surface 18 and mating threading 124 on needle cover storage attachment segment 56. Thus, body neck 16 and needle cover 40 must be sized and constructed to enable such threaded mating attachment.

In an alternative preferred embodiment as shown in FIG. 3, storage attachment means 120 comprises at least one rib 126 on body neck inner surface 18 and at least two ribs 128 on needle cover storage attachment segment 56. Body neck rib 126 and needle cover ribs 128 are sized and constructed so that body neck rib 126 may be selectively "snapped" into and out of place from between needle cover ribs 128. When body neck rib 126 is snapped into place in between needle cover ribs 128, body neck rib 126 is securely held therebetween thereby also securing needle cover 40 to body neck 16 and syringe body 10. It is understood that the installation of rib 126 and ribs 128 may be inverted so that body neck inner surface 18 includes at least two ribs and needle cover storage attachment segment includes at least one rib.

In addition, the relevant parts of either embodiment of storage attachment means 120 must be sized and constructed so that their mating attachment is sufficiently tight and restrictive to provide a seal on body neck 16 thereby prohibiting flow of solution 11 from the syringe body interior 13 to the exterior of syringe body 10. It is understood that the preferred abutment of body neck front surface 22 to needle cover shoulder 54 when syringe 5 is in the storage position 170 also aids in providing the sealing attachment between needle cover 40 and body neck 16.

Operational attachment means 160 selectively attaches needle 80 to syringe body 10 for operation of syringe 5. In the preferred embodiment, operational attachment means 160 comprises the substantially equal diameter lengths of needle cylinder inner surface 88 and body neck outer surface 20. Thus, body neck 16 can be inserted into and can frictionally retain needle cylinder 86.

IN OPERATION

It is important to note that, in syringe 5, storage attachment means 120 attaches needle cover 40 to syringe body neck 16 so that at least a portion of needle cover 40 is located within the interior 13 of a pre-filled syringe body 10. Thus, initially, syringe body 10 is pre-filled with solution 11, storage attachment means 120 sealingly attaches body neck inner surface 18 to the storage attachment segment 56 of needle cover 40, needle cover shoulder 54 is adjacent to, but preferably abuts, body neck front surface 22, and the portion of needle cover 40 from storage attachment segment 56 to needle cover first end 42 is located within the interior 13 of syringe body 10 and is surrounded by solution 11. As previously disclosed, needle 80 is securely retained within needle cover 40. In addition, because storage attachment means 120 is a sealing attachment, solution 11 does not escape through body neck 16. This initial position of syringe 5 and needle cover 40 is referred to as storage position 170 and is shown in FIGS. 1–3.

When a user is prepared to operate syringe 5, the user must move needle cover 40 (with needle 80 retained therein) from its storage position 170 to its operative position 172. The operative position 172 of syringe 5 and needle cover 40, shown in FIG. 4, corresponds to the well-known relative position of a syringe body and its needle when the syringe is ready for use. In the operative position 172, operational attachment means 160 selectively attaches body neck outer surface 20 to needle cylinder inner surface 88, and needle puncture end 82 is distal to syringe body 10.

In order to move needle cover 40 from storage position 170 to operative position 172, the user must first disengage storage attachment means 120. In the embodiment in which storage attachment means 120 comprises mating body neck threading 122 and needle cover threading 124, the user simply "unscrews" the threaded engagement between body neck 16 and needle cover 40. In the embodiment in which storage attachment means 120 comprises body neck rib 126 and needle cover ribs 128, the user need only pull and "un-snap" the ribbed engagement between body neck 16 and needle cover 40.

Once storage attachment means 120 is disengaged, the user should pull needle cover 40 from within the interior 13 of syringe body 10. This pulling motion should be performed carefully so that solution 11 does not spill out of the interior 13 of syringe body 10 through now uncovered body neck 16. Thus, preferably, this pulling motion, as well as the disengagement of storage attachment means 120, is performed with syringe body 10 in a vertical position and with body end 12 (including body neck 16) at the top position.

After pulling needle cover 40 completely from within syringe body 10, the user should reverse or flip needle cover 40 so that needle cover second end 44 is adjacent body neck 16. As previously disclosed, during the preceding operations, needle 80 is securely held within needle cover 40. Next, the user moves needle cover second end 44 towards syringe body 10 so that body neck 16 is inserted within needle cylinder 86. Because the diameter of body neck outer surface 20 is substantially equal to the diameter of needle cylinder inner surface 88, needle 80 is frictionally securely held on body neck 16. Operational attachment means 160 thus attaches needle 80 to syringe body 10. At this point, needle 80 and needle cover 40 are essentially in their operative position 172.

To better enable operational attachment means 160, in one embodiment (not shown in the Figures), needle 80 and needle cover 40 are sized so that, when needle 80 is retained within needle cover 40, needle attachment end 84 extends past needle cover second end 44.

Finally, the user should pull needle cover 40 from needle 80. In order to do so without also pulling needle 80 from its operative connection to body neck 16 (ie., disengaging operational attachment means 160), necessarily, the friction retaining needle 80 within needle cover 40 must be less than the friction holding needle 80 to body neck 16. Thus, needle cover 40, needle 80, and body neck 16, and their corresponding parts, must be sized and constructed accordingly. After removing needle cover 40 from needle 80, syringe 5 is ready for use as widely known in the prior art.

After syringe 5 is utilized, the user can reverse the steps described herein and move needle cover 40 and needle 80 from their operative position 172 into their storage position 170. Thus, the user first disengages operational attachment means 160 by removing needle 80 from syringe body neck 16. Next, the user reinserts needle 80 into needle cover 40 as described herein. And finally, with needle 80 securely retained within needle cover 40, the user re-engages storage attachment means 120. The syringe 5 will therefore be back to its storage position 170 and the needle puncture end 82 will be safely enclosed within needle cover first end 42 inside of syringe body 10. With needle puncture end 82 safely enclosed, the user may then dispose of used syringe 5.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

I claim:

1. A pre-filled syringe, comprising:
   a syringe body, said syringe body having a partially open end;
   a needle:
   a hollow needle cover;
   said needle selectively retained within said needle cover;

a storage attachment means selectively sealingly attaching said needle cover to said body through said body open end so that at least a portion of said needle cover is located within said syringe body;

said storage attachment means thereby defining a storage position for said syringe when said storage attachment means is engaged;

an operational attachment means selectively attaching said needle to said syringe body for operation of said syringe;

said operational attachment means thereby defining an operative position for said syringe when said operational attachment means is engaged;

the majority of said needle cover located within said syringe body when said syringe is in said storage position;

wherein said needle includes a needle puncture end and a needle attachment end;

said needle cover includes a closed needle cover first end and an open needle cover second end;

said needle cover first end corresponds to and selectively houses said needle puncture end when said needle is retained within said needle cover;

said needle cover second end corresponds to and selectively houses said needle attachment end when said needle is retained within said needle cover;

said needle cover first end located within said syringe body when said syringe is in said storage position;

said needle cover second end located exterior to said syringe body when said syringe is in said storage position;

said syringe body further includes a syringe body opening on said syringe body partially open end;

said syringe body further includes a syringe body neck extending from the perimeter of said syringe body opening in a direction away from said syringe body;

said needle cover further includes a needle cover shoulder and a needle cover outer surface;

said needle cover shoulder located proximate said needle cover second end;

said needle cover outer surface having a cross-sectional area;

said needle cover outer surface cross-sectional area being generally uniform from said needle cover second end to said needle cover shoulder;

said needle cover outer surface cross-sectional area decreasing at said needle cover shoulder;

said needle cover outer surface cross-sectional area gradually decreasing from needle cover shoulder to said needle cover first end;

said syringe body neck includes a front surface located distal to said syringe body; and said needle cover shoulder abuts said body neck front surface when said syringe is in said storage position.

2. A syringe as in claim 1, wherein:

said needle cover further includes a needle cover storage attachment segment;

said needle cover storage attachment segment located on said needle cover outer surface;

said syringe body neck further includes a syringe body neck inner surface; and said needle cover storage attachment segment located directly adjacent to said body neck inner surface when said syringe is in said storage position.

3. A syringe as in claim 2, wherein said storage attachment segment is located intermediate said needle cover shoulder and said needle cover first end, directly adjacent to said needle cover shoulder.

4. A syringe as in claim 3, wherein said storage attachment means comprises:

said syringe body neck inner surface including at least one rib extending therefrom;

said needle cover storage attachment segment including at least two ribs extending therefrom;

said at least one syringe body neck inner surface rib and said at least two needle cover storage attachment segment ribs sized and constructed so that said at least one syringe body neck inner surface rib is selectively snapped into and out of place from between said at least two needle cover storage attachment segment ribs; and said at least one syringe body neck inner surface rib being securely held by said at least two needle cover storage attachment segment ribs when positioned therebetween thereby attaching said needle cover to said syringe body.

5. A syringe as in claim 3, wherein said storage attachment means comprises:

said needle cover storage attachment segment including at least one rib extending therefrom;

said syringe body neck inner surface including at least two ribs extending therefrom;

said at least two syringe body neck inner surface ribs and said at least one needle cover storage attachment segment rib sized and constructed so that said at least one needle cover storage attachment segment rib is selectively snapped into and cut of place from between said at least two syringe body neck inner surface ribs; and said at least one needle cover storage attachment segment rib being securely held by said at least two syringe body neck inner surface ribs when positioned therebetween thereby attaching said needle cover to said syringe body.

6. A syringe as in claim 3, wherein said storage attachment means comprises:

said needle cover attachment segment including threading thereon;

said syringe body neck inner surface including threading thereon; and said needle cover attachment segment threading selectively mating with said syringe body neck inner surface threading thereby attaching said needle cover to said syringe body.

7. A syringe as in claim 3, wherein, when said syringe is in said operative position:

said needle attachment end is selectively attached to said syringe body neck; and said needle puncture end is distal to said syringe body.

8. A syringe as in claim 7, wherein:

said needle includes a cylinder adjacent said needle attachment end;

said needle cylinder includes an inner surface;

said syringe body neck further includes an outer surface;

said needle cylinder inner surface having a cross-sectional diameter;

said syringe body neck outer surface having a cross-sectional diameter; and said operational attachment means comprises the substantially equal cross-sectional diameter lengths of said needle cylinder inner surface and said syringe body neck outer surface so that said needle cylinder is selectively securely received by said syringe body neck.

9. A syringe as in claim 8, wherein:

said needle cylinder includes an outer surface;

said needle cylinder outer surface having a cross-sectional area;

said needle cover includes an inner surface;

said needle cover inner surface having a cross-sectional area; and said needle cover cylinder outer surface cross-sectional area being substantially equal to said needle cover inner surface cross-sectional area at said needle cover second end so that said needle is selectively inserted and thereby frictionally retained within said needle cover.

10. A syringe as in claim 9, wherein said needle attachment end extends past said needle cover second end when said needle is selectively retained within said needle cover.

11. A syringe as in claim 9, wherein:

said syringe body neck outer surface, said needle cylinder inner surface, said needle cylinder outer surface and said needle cover inner surface are sized and constructed according to their respective said cross-sectional area such that the frictional retention of said needle cylinder on said syringe body neck is stronger than the frictional retention of said needle within said needle cover;

whereby said needle cover is selectively removable from within said needle when said operational attachment means is engaged without also removing said needle cylinder from said syringe body neck.

* * * * *